(12) United States Patent
Willis

(10) Patent No.: US 7,448,874 B2
(45) Date of Patent: Nov. 11, 2008

(54) APPARATUS AND METHOD TO MONITOR BODY TEMPERATURE

(75) Inventor: Richard Andrew Willis, Arlington, TN (US)

(73) Assignee: Martha J. Willis Revokable Living Trust, Millington, TN (US)

( * ) Notice: Subject to any disclaimer, the term of this patent is extended or adjusted under 35 U.S.C. 154(b) by 141 days.

(21) Appl. No.: 11/407,516

(22) Filed: Apr. 19, 2006

(65) Prior Publication Data

US 2006/0235328 A1    Oct. 19, 2006

Related U.S. Application Data

(60) Provisional application No. 60/672,747, filed on Apr. 19, 2005.

(51) Int. Cl.
*H01R 33/00* (2006.01)

(52) U.S. Cl. ........................................ 439/37

(58) Field of Classification Search .................. 439/37, 439/630, 492–499, 354; 455/333, 309; 340/870, 340/16; 43/1; 2/458, 69; 600/388, 547, 600/549

See application file for complete search history.

(56) References Cited

U.S. PATENT DOCUMENTS

| | | | |
|---|---|---|---|
| 4,747,413 A | 5/1988 | Bloch | 128/736 |
| 4,763,112 A | 8/1988 | Hsieh | 340/573 |
| 5,244,397 A * | 9/1993 | Anhalt | 439/101 |
| 5,546,955 A | 8/1996 | Wilk | 128/736 |
| 5,634,468 A | 6/1997 | Platt et al. | 128/696 |
| 5,726,631 A * | 3/1998 | Lin | 340/573.1 |
| 5,802,611 A * | 9/1998 | McKenzie et al. | 2/69 |
| 5,810,620 A * | 9/1998 | Kobayashi et al. | 439/610 |
| 6,047,203 A * | 4/2000 | Sackner et al. | 600/388 |
| 6,080,690 A | 6/2000 | Lebby et al. | 442/209 |
| 6,165,006 A * | 12/2000 | Yeh et al. | 439/490 |
| 6,238,354 B1 | 5/2001 | Alvarez | 600/549 |
| 6,547,745 B1 | 4/2003 | Rubinstein | 600/549 |
| 6,605,038 B1 * | 8/2003 | Teller et al. | 600/300 |
| 6,612,877 B2 * | 9/2003 | Hyland | 439/676 |
| 6,687,523 B1 * | 2/2004 | Jayaramen et al. | 600/388 |
| 6,783,926 B2 * | 8/2004 | Reece | 430/630 |
| 6,839,035 B1 * | 1/2005 | Addonisio et al. | 343/742 |
| 6,897,788 B2 * | 5/2005 | Khair et al. | 340/870.16 |
| 7,004,910 B2 | 2/2006 | Lindsey | 600/549 |
| 7,016,661 B2 * | 3/2006 | Gorday et al. | 455/309 |
| 2002/0013538 A1 | 1/2002 | Teller | 600/549 |
| 2004/0034289 A1 | 2/2004 | Teller et al. | |

FOREIGN PATENT DOCUMENTS

GB      2 416 924      2/2006

* cited by examiner

*Primary Examiner*—Alexander Gilman
(74) *Attorney, Agent, or Firm*—Butler, Snow, O'Mara, Stevens & Cannada PLLC

(57) ABSTRACT

An apparatus is provided which is made of a garment having at least one connector to receive an electronic transmission module and an electronic monitor configured to remotely receive and control electronic transmission from the electronic transmission module. The garment includes a sensor to detect the temperature of the wearer. This invention also provides a connector for making an electrical connection. This invention also provides a method for monitoring the body temperature of the wearer.

10 Claims, 8 Drawing Sheets

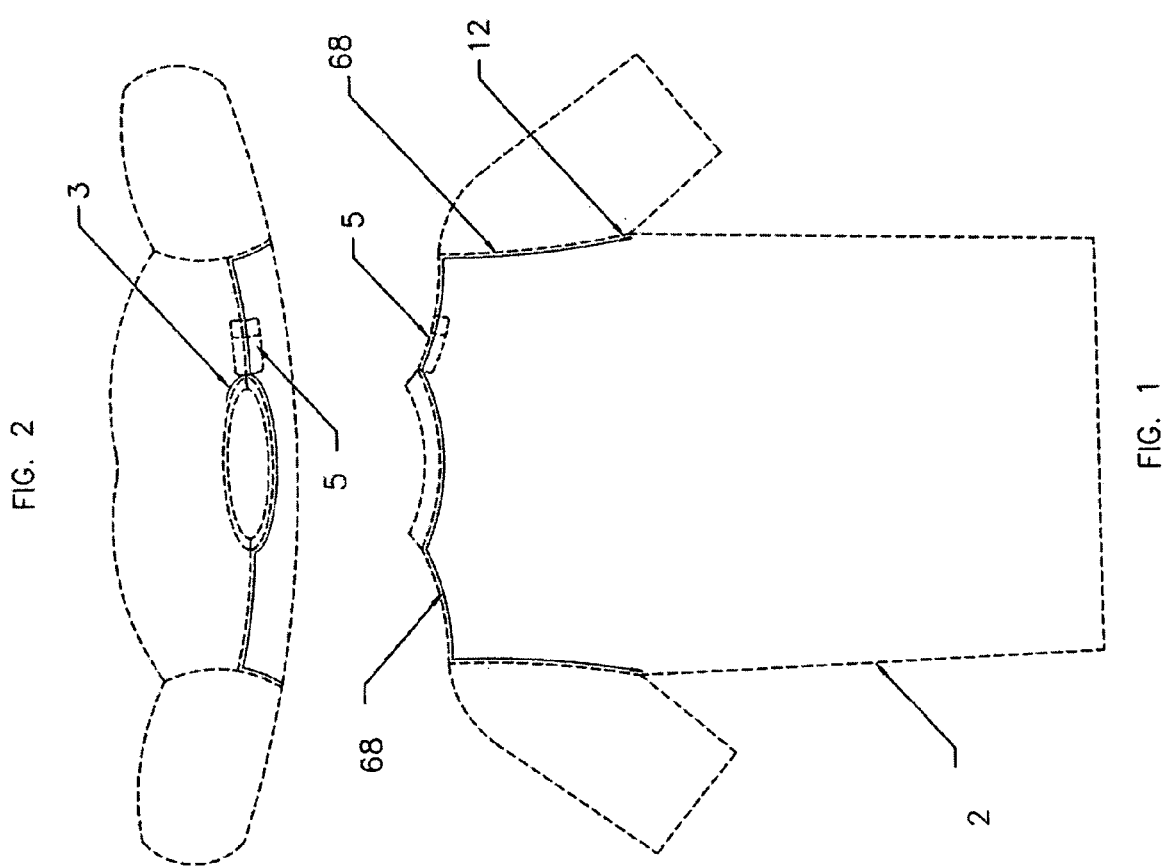

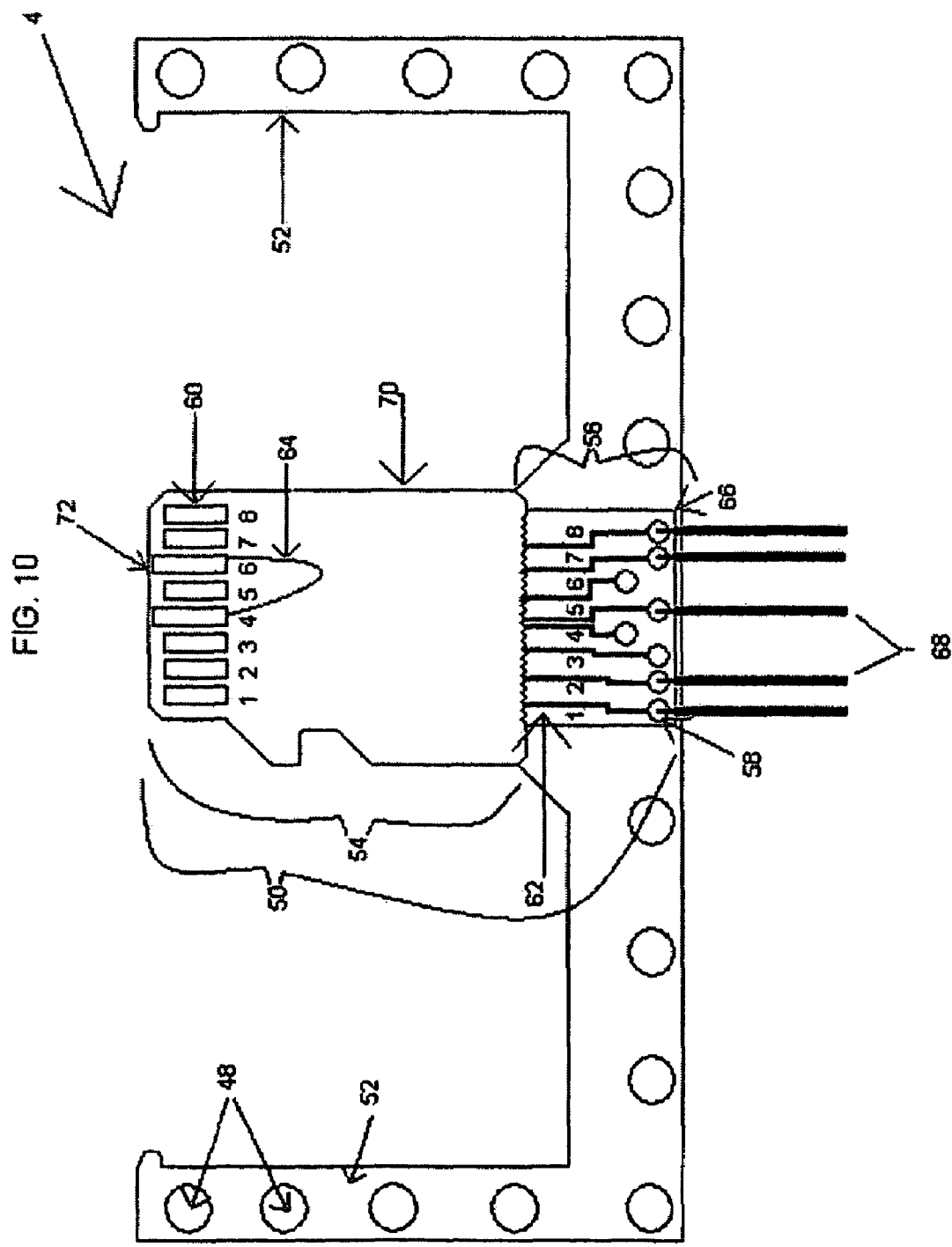

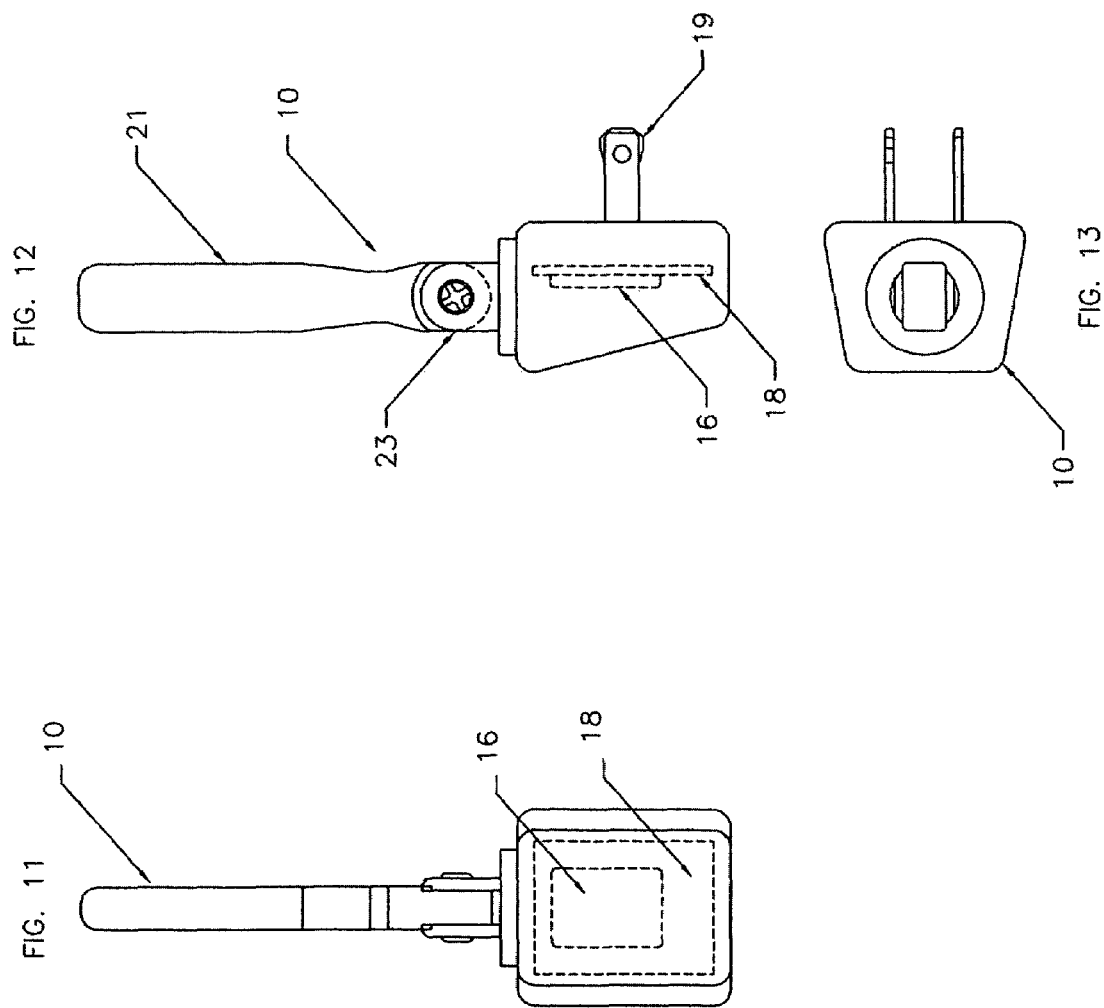

APPARATUS AND METHOD TO MONITOR BODY TEMPERATURE

RELATED APPLICATIONS

This application claims the benefit of prior Provisional Application Ser. No. 60/672,747 under 35 U.S.C. § 119 (e) and is hereby specifically incorporated by reference in its entirety

STATEMENT REGARDING FEDERALLY SPONSORED RESEARCH OR DEVELOPMENT

Not Applicable

REFERENCE A "MICROFICHE APPENDIX"

Not Applicable

FIELD OF THE INVENTION

This invention relates to an apparatus and method to monitor body temperature.

BRIEF SUMMARY OF THE INVENTION

An apparatus is provided that is made of a garment, at least one connector attached to the garment and an electronic transmission module connected to the connector. The connector is configured to receive an electronic transmission module. The electronic transmission module is programmed for wireless transmission.

In one embodiment, the apparatus has a sensor positioned in the garment to obtain a temperature reading of a wearer of the garment. In one embodiment, the apparatus has a means to communicate the temperature reading to the electronic transmission module. In one embodiment, the apparatus has an electronic monitor to remotely receive and control electronic transmission for the electronic transmission module.

In one embodiment, the electronic monitor has a device that conforms to the IEEE 802.15.4 Low-Rate Wireless Personal Area Standard. In one embodiment, the electronic transmission module has a device that conforms to the IEEE 802.15.4 Low-Rate Wireless Personal Area Standard.

In one embodiment, the apparatus has a means to extend the electronic transmission range of the electronic transmission module. In one embodiment, the means to extend the electronic transmission range of the electronic transmission module is a range extender. The range extender has a device that conforms to the IEEE 802.15.4 Low-Rate Wireless Personal Area Standard.

A connector is provided for making an electrical connection upon insertion of the connector into a corresponding receiver. The receiver has a plurality of connection pads. At least one of the connection pads of the receiver is connected to a power source. The connector is made of an extended body which has an insertion portion and non-insertion portion. The non-insertion portion has a plurality of solder points. The insertion portion has a plurality of connecting pads. The connecting pads on the insertion portion of the connector correspond to the connecting pads on the receiver. The connector is also made of at least one wire attached to the solder points, at least one trance connecting the at least one wire to at least one pad of the connector, and at least one looping trace connecting at least two connection pads of the connector.

In one embodiment, the connector has two side members contiguous to the non-insertion portion the body. In an embodiment, the extended body is a printed circuit board.

A method is provided for monitoring the body temperature of an individual. The method consists of the following steps: (a) placing a garment on an individual, wherein the garment has at least one sensor positioned to obtain a body temperature reading of the individual, wherein the garment has a connector configured to receive an electronic transmission module, wherein the electronic transmission module is programmed for electronic transmission; (b) securing an electronic transmission module into the connector which is configured to receive an electronic transmission module; (c) determining a body temperature from the sensor; (d) communicating the body temperature from the individual to an electronic monitor over a local wireless connection, wherein the electronic monitor is configured to remotely receive and control electronic transmission from the electronic transmission module; and (e) displaying the body temperature on the electronic monitor.

In one embodiment, the method comprising the step of extending the electronic transmission range between the electronic transmission module and the electronic monitor with a range extender.

BRIEF DESCRIPTION OF THE DRAWINGS

FIG. 1 is a schematic rear view of a garment to monitor body temperature.

FIG. 2 is a schematic top view of a garment to monitor body temperature.

FIG. 10 is an enlarged view of the connector with a cut away portion showing the printed circuit board.

FIG. 11 is a schematic front view of a range extender.

FIG. 12 is a schematic side view of the range extender.

FIG. 13 is a schematic top view of the range extender.

DETAILED DESCRIPTION OF THE INVENTION

Figures 3, 4, 5, 6:
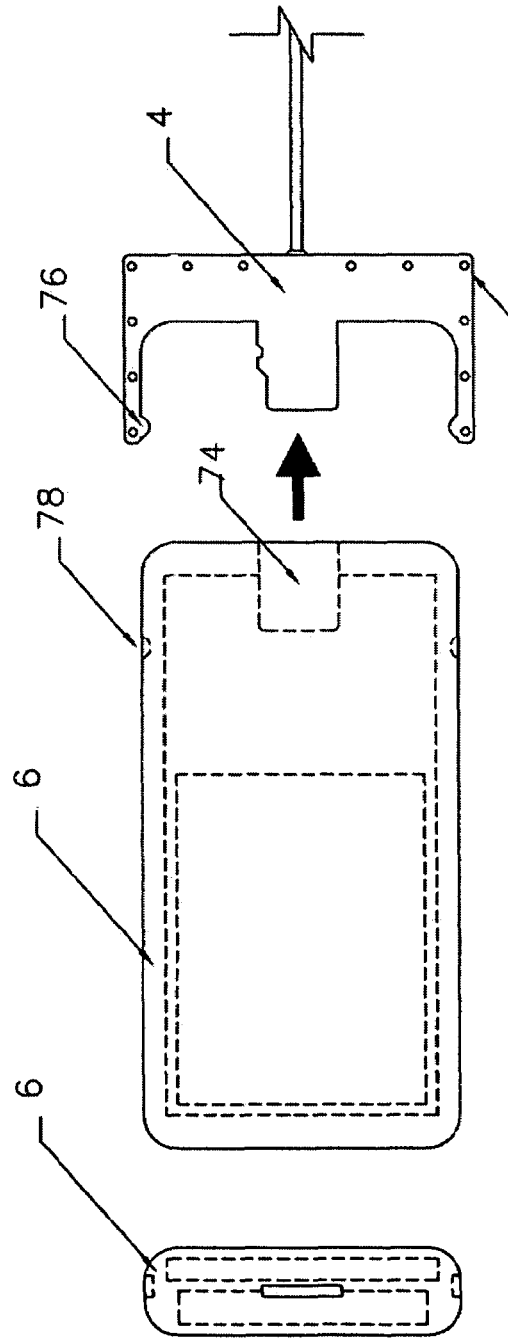
FIG. 3 is a side view of an electronic transmission module.
FIG. 4 is a side view of an embodiment of a connector to receive an electronic module.
FIG. 5 is a vertical top view of an electronic transmission module.
FIG. 6 shows a schematic view of the assembly process involving an electronic transmission module inserted into a connector to receive an electronic module.

Referring to FIGS. 1-9, an embodiment of apparatus 1 to monitor body temperature is disclosed. The apparatus 1 is made of garment 2, connector to receive an electronic transmission module 4, electronic transmission module 6, and electronic monitor 8.

Referring now to FIGS. 1-2, garment 2 can be made of any material that will allow garment 2 to fit snuggly against the body of the wearer. Spandex is one example of a material, however other materials, such as a polyester elastane blend, may be used as desired by one of skill in the art. The material of garment 2 has elasticity properties that keep it close to the body of the wearer and such properties prevent garment 2 from stretching out and loosing its conformity to the body.

In one embodiment, garment 2 has thermal sensors 12 sewn into garment 2 in such a way that the sensors 12 are held in close proximity to the body in the area of the underarms. In one embodiment, the sensors 12 are General Electric MA 100™ (GE Thermometrics, Inc. Billerica, Mass.) thermistors but any other sensors that are capable of measuring temperature changes can be used as desired by one of skill in the art. In an embodiment, garment 2 has two sensors 12 but any number of sensors can be used, including one, as desired by one of ordinary skill in the art. In one embodiment, sensors 12 are encased in garment 2 in the area of the underarms, however, sensors 12 may be placed at other locations where such sensors can obtain temperature reading as desired by one of skill in the art.

Two connection wires 68 are connected to each sensor 12. Connection wires 68 are encased in garment 2 in such a way that the each wire 68 travels from the sensor 12 to the connector 4. In one embodiment, connection wires 68 travel and are encased along the seams of garment 2. Garment 2 has antenna 3 appropriate to allow electronic transmission between electronic transmission module 6 and electronic monitor 8. Antenna 3 is located in the collar of garment 2. Antenna 3 is appropriate to the IEEE 802.15.4 Standard.

Referring to FIGS. 1-2 and 10, connector 4 is fixedly attached to garment 2. In one embodiment, connector 4 is located in pocket 5 located near the collar of garment 2. Connector 4 is attached to garment 2 by sewing connector 4 to garment 2. Connector 4 has sewing holes 48 for such attachment (See FIG. 6). Other forms of attaching connector 4 may be used as desired by one of skill in the art. In one embodiment, connector 4 is attached to the top shoulder area of garment 2 near the collar but connector 4 can be attached to garment 2 anywhere as desired by one of ordinary skill in the art. Connector 4 is made of a sturdy, water resistant material such as a polymer or plastic but other materials may be used as desired by one of ordinary skill in the art.

Referring now to FIG. 10, a cut away view of connector 4 is shown. Connector 4 has the size and connection specifications of the male portion of the Micro SD. Other size and connection specification may be used as desired by one of ordinary skill in the art. Connector 4 does not contain an electronic data storage device as contained in the Micro SD. Instead connector 4 is configured to allow connector 4 to make an electrical connection with module 6 upon assembly of module 6 and connector 4. Connector 4 has an extended body 50 that allows for the physical attachment of connector 4 to receiver 74 of module 6. (See FIG. 6). In one embodiment, connector 4 has side members 52 that allow connector 4 to be attached to another object, such as garment 2. Body 50 of connector 4 has an insertion portion 54 and a non-insertion portion 56. Housing 70 covers and protects connector 4; however, the connection pads 60 of body 50 are not covered by housing 70. Connection pads 60 are at the front connection edge of connector 4. Housing 70 is made of a sturdy, water resistant material such as a polymer or plastic but other materials may be used as desired by one of ordinary skill in the art. Insertion portion 54 has eight connection pads or tabs 60. Connection pads 60 are metallic connectors. In one embodiment, two of the connection pads 60 are connected by a looping trace 64. Non-insertion portion 56 has solder points 58. In one embodiment, five wires 68 are attached to five solder points 58 of non-insertion portion 56. Traces 62 connect connection wires 68 to connection pads 60. In one embodiment, connector 4 has snap tabs 76 that snap into snap notches 78 when connector 4 and module 6 are assembled thus reinforcing the assembly between connector 4 and module 6.

Referring to FIGS. 3 and 6, module 6 has a receiver 74. Receiver 74 is reversibly connected to module 6. Receiver 74 has the size and connection specifications of the female portion of the Micro SD. Other size and connection specifications may be used as desired by one of ordinary skill in the art. Receiver 74 has eight connection pads that correspond to the connection pads 60 of connector 4. Connection pads of receiver 74 are metallic. Receiver 74 is connected to power supply 20.

Referring again to FIG. 10, body 50 is a printed circuit board 66. In one embodiment, the printed circuit board 66 has five connection wires 68 permanently affixed to board 66. Two wires 68 (one receiving wire and one transmitting wire) connect to one sensor 12, two wires 68 (one receiving wire and one transmitting wire) connect to a second sensor 12, and one wire which connects to antennae 3 that enables the electronic transmission module 6 to transmit information to electronic monitor 8. The connection wires 68 are insulated except at the point of attachment to board 66. Housing 70 encases wires 68 as wires 68 exit connector 4 so that moisture is kept out of the internal workings of connector 4.

Referring now to FIGS. 1-2, 3, 5 and 6, apparatus 1 has an electronic transmission module 6 that connects to connector 4. Electronic transmission module 6 contains a device 17 that conforms to the IEEE 802.15.4 Low-Rate Wireless Personal Area Standard or to the ZigBee Protocol. ZigBee is a published specification set of high level communication protocols designed to use small, low-power digital radios based on the IEEE 802.15.4 standard for wireless personal area networks. In one embodiment, electronic transmission module 6 is a ZigBee End Device. Pursuant to ZigBee Protocol, module 6 has the functional capabilities to communicate with monitor 8. In one embodiment, module 6 cannot relay data from other ZigBee devices. In another embodiment, module 6 can relay data from other ZigBee devices, wherein module 6 serves as a ZigBee Router Device.

Device 17 of module 6 contains a radio and a microprocessor which contains the code that enables sensor 12 to constantly measure the temperature of the individual wearing garment 2 upon assembly of module 6 into connector 4. The microprocessor within device 17 also contains the code that enables the radio of device 17 to function within the specification set forth by the ZigBee 1.0 specifications and subsequent developed versions of such specifications. Electronic transmission module 6 has a power supply 20 (See FIG. 3). In one embodiment, power supply 20 is a battery.

Upon assembly of module 6 and connector 4, eight connection pads 60 of connector 4 line up and connect to eight connection pads located in receiver 74 of module 6. One of the pads located inside receiver 74 is connected to the power supply 20 of module 6. This connection is accomplished by a printed circuit board trace between such connection pad inside receiver 74 and power supply 20. The terminal of power supply 20 is affixed to a point on the printed circuit board inside module 6. This physical connection allows the electrical current from the power supply 20 to flow from the power supply 20 to such connection pad inside receiver 74. The electrical current then passes from the pad inside receiver 74 to the corresponding connection pad 60 on connector 4. The corresponding connection pad 60 on connector 4 has a looping trace 64 connecting such pad 60 to a second connection pad 60 located on connector 4, thus connecting second connection pad 60 and the corresponding pad inside receiver 74 connected to power-in trace creating a power circuit that allows all electronic components of the module 6 to operate.

Upon assembly of the module 6 and connector 4, an electrical connection turns module 6 "on" and module 6 sends out a signal to electrical monitor 8 (described below). The electrical connection also enables module 6 to communicate with sensors 12 directing sensors 12 to measure the temperature of the body of the wearer of garment 2. The electrical connection also enables module 6 to make the connection to antenna 3 which allows the module 6 to transmit electronic communication to the electronic monitor 8.

Figure 7:
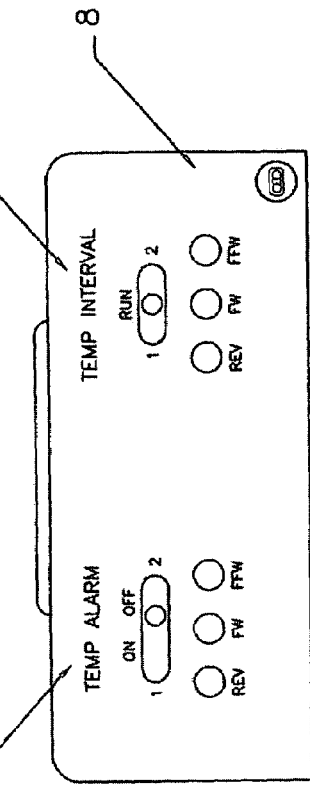
FIG. 7 is a side view of an electronic monitor.
Figure 8:
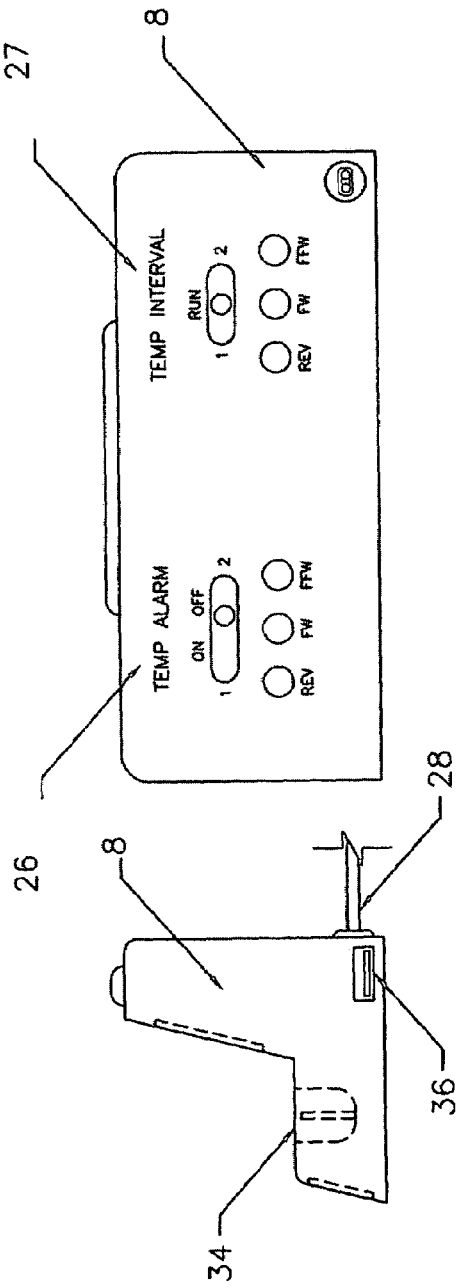
FIG. 8 is a rear view of an electronic monitor.
Figure 9:
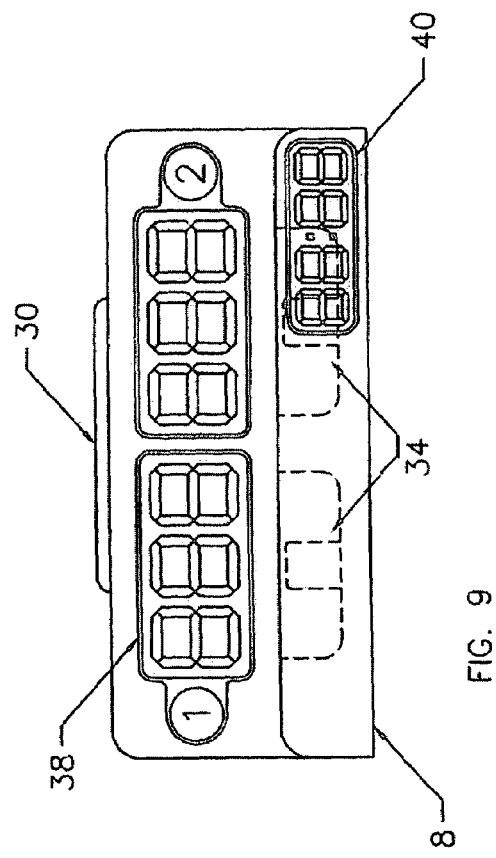
FIG. 9 is a front view of an electronic monitor.

Referring now to FIGS. 7-9, apparatus 1 has an electronic monitor 8 that is configured to remotely receive and control electronic transmission from electronic transmission module 6. Electronic monitor 8 has a radio that conforms to the IEEE 802.15.4 Low-Rate Wireless Personal Area Standard. Electronic monitor 8 has a microprocessor that operates in accordance with ZigBee 1.0 specifications and subsequently developed versions of such specifications. The ZigBee specifications dictate the communications received and controlled by electronic monitor 8.

Monitor 8 serves as a Coordinator Device in the ZigBee Mesh Network. Electronic monitor 8 will dictate the frequency of temperature readings and transmissions from the electronic transmission module 6. Monitor 8 has frequency control option 27. Electronic monitor 8 contains code that allows the user of apparatus 1 to setup parameters of temperature profiles that trigger audible and visible alarms set off by the electronic monitor 8 when those parameters are met or exceeded. Monitor 8 has alarm control option 26. Electronic monitor 8 may also contain code that initiates other message activities over the public or a private telephone network, radio or intercom network as well as create messages for electronic communications such as email.

Monitor 8 contains code that allows the temperature readings to be recorded to flash memory for later retrieval through a port or by removal of the flash device. In one embodiment, a USB port 36 is used to retrieve temperature readings but any other port can be used as desired by one of ordinary skill in the art (See FIG. 7).

Monitor 8 may communicate with more than one electronic transmission module 6 inserted into the connector 4 of two garments 2 within its Mesh Network. Referring to FIG. 9, monitor 8 has two temperature reading displays 38. Monitor 8 has two charging circuits 34 for recharging electronic transmission module 6 (See FIG. 9). In one embodiment, monitor 8 has an alarm suspend 30 and clock 40. Monitor 8 has a commercial plug attachment 28 built into it allowing the user to plug the monitor 8 into commercial power.

Referring now to FIGS. 11-12, in one embodiment, apparatus 1 has a range extender 10 that extends the electronic transmission range of the electronic transmission module 6. If module 6 and monitor 8 exceed the operable range, appropriate to the IEEE 802.15.4 Standard, the range extender 10 can be used to extend the range and allow the apparatus 1 to function. The range extender 10 has a radio 16 that conforms to IEEE 802.15.4 Low Rate Wireless Personal Area Standard and range extender 10 has a microprocessor 18 coded with ZigBee 1.0 specifications and subsequently developed specifications. The range extender 10 serves as a ZigBee router. Range extender 10 is connected to a power supply through outlet 19 and has antenna 21. Antenna 21 is connected to extender 10 by hinge 23. Antenna 21 is appropriate to the IEEE 802.15.4 Standard. The radio in the range extender 10 follows the ZigBee protocols under the "Router" functional specification. The range extender 10 allows electronic transmission module 6 to be bridged to electronic monitor 8 if it is out of range or if some other force precludes the proper communication between the electronic transmission module 6 and electronic monitor 8.

Figure 14:
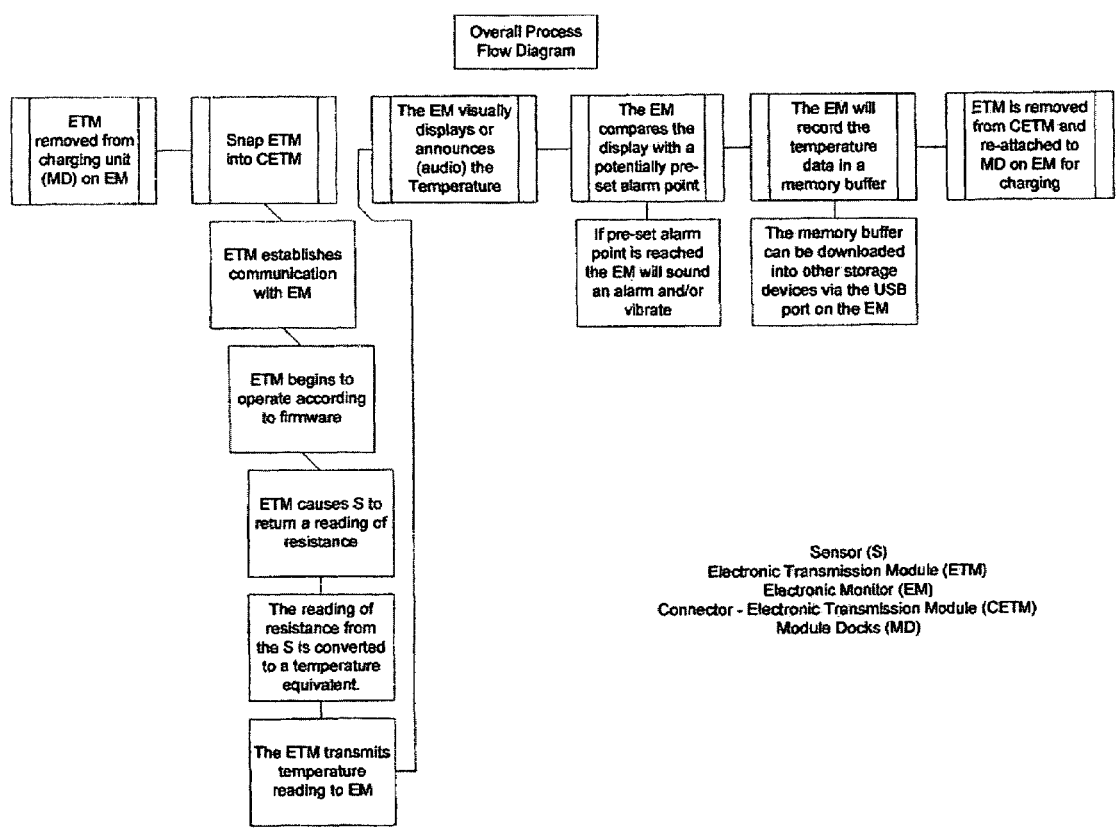
FIG. 14 is a flow chart of the process to monitor body temperature.

Referring now to FIG. 14 with reference to FIGS. 1-10, the overall process of monitoring body temperature of an individual is provided. Module 6 is removed from charging circuit or unit 34. Module 6 is snapped into connector 4. Upon assembly, module 6 communicates with monitor 8 and module 6 begins operating according to firmware or code. Module 6 causes sensor 12 to return a reading of resistance which is converted to a temperature equivalent. Module 6 transmits the temperature reading to monitor 8 which displays or announces the temperature. Monitor 8 compares the display with a potentially pre-set alarm point. If the pre-set alarm point is reached, monitor 8 will sound an alarm and/or vibrate. Monitor 8 records the temperature data in a memory buffer which can be downloaded into other storage devices via the port on monitor 8. Module 6 is removed from the connector 4 and re-attached to charging circuit or unit 34 on monitor 8 for charging. The process can be started again once module 6 is recharged.

Figure 15:
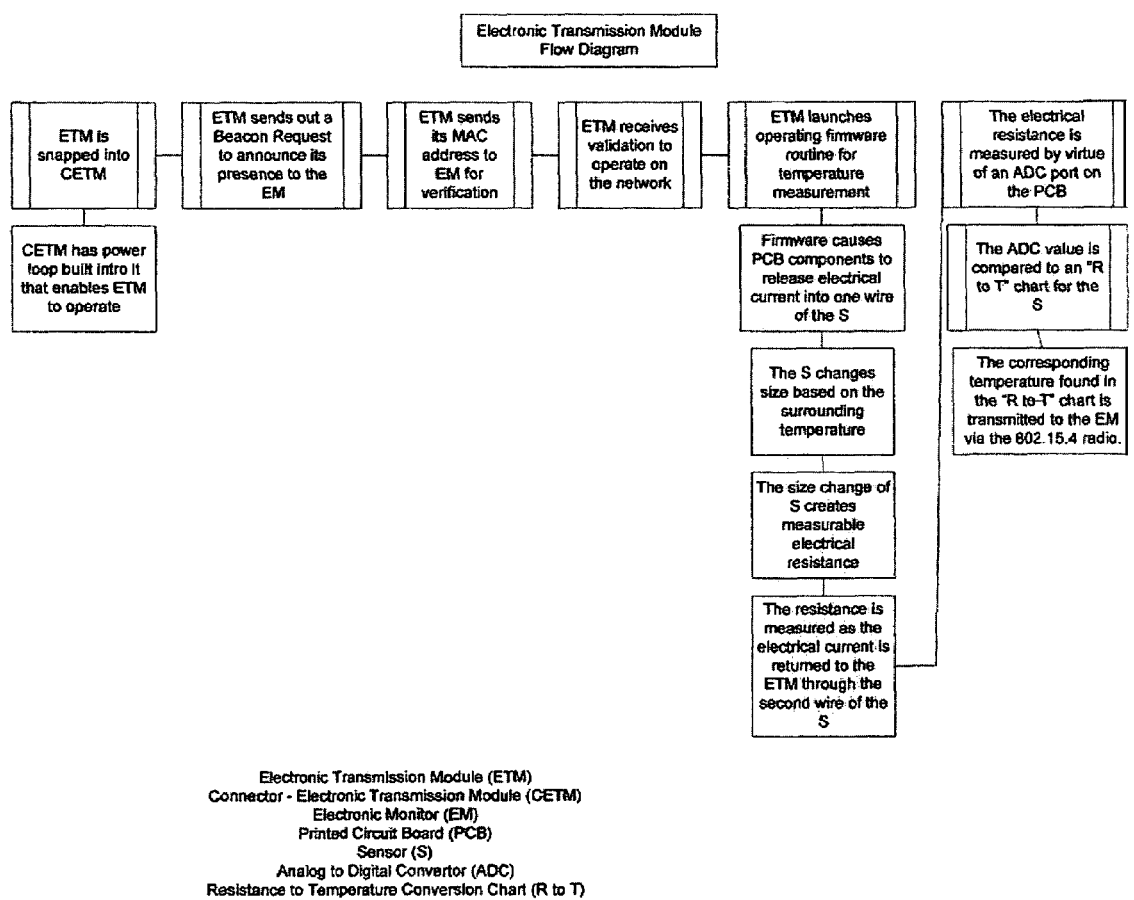
FIG. 15 is a flow chart of the internal workings of the electronic transmission module.

Referring now to FIG. 15 with reference to FIGS. 1-10, the internal workings of the electronic transmission module 6 are provided. Module 6 is snapped into connector 4 which has looping trace 64 that enables module 6 to operate. Module 6 sends out a beacon request to announce its presence to monitor 8. Module 6 sends its MAC address to monitor 8 for verification. Module 6 receives validation to operate on network. Module 6 launches operating firmware routine for temperature measurement. Firmware causes printed circuit board components to release electrical current into one wire of sensor 12. Sensor 12 changes size based on the surrounding temperature. The size change of sensor 12 creates measurable electrical resistance. The resistance is measured as the electrical current is returned to module 6 through the second wire of the sensor. The electrical resistance is measured by virtue of an ADC port on the printed circuit board. The ADC value is compared to an "R to T" chart for sensor 12. The corresponding temperature found in the "R to T" chart is transmitted to monitor 8 via the 802.15.4 radio.

Figure 16:
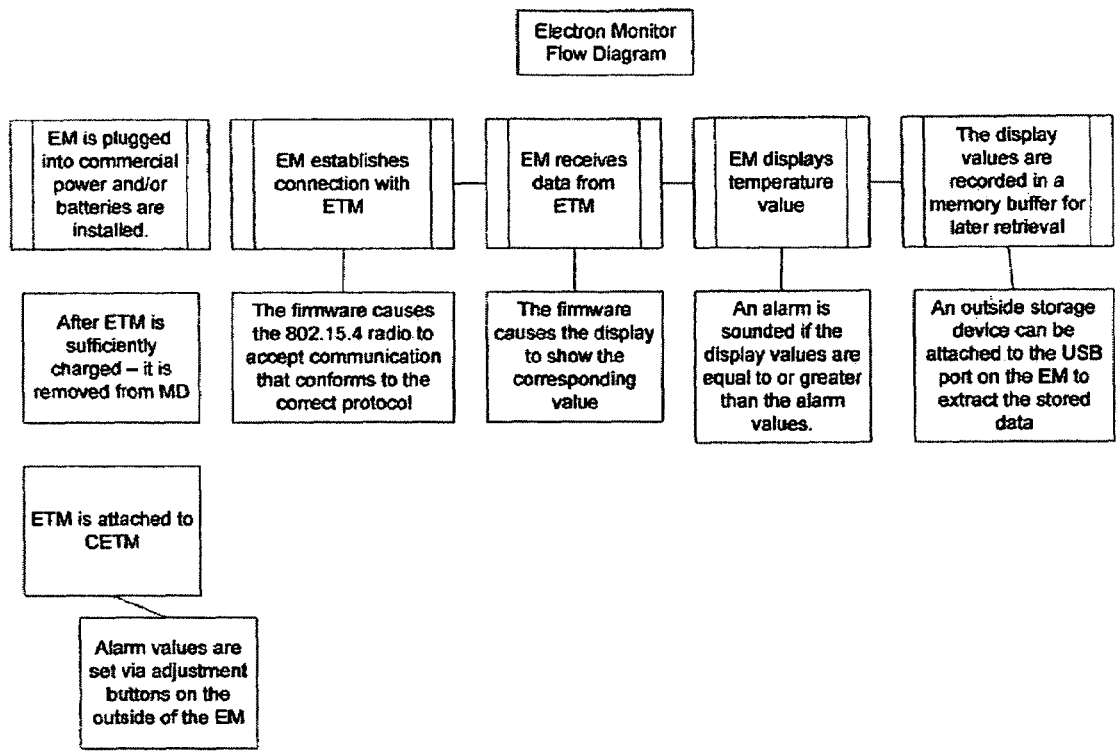
FIG. 16 is a flow chart of the internal workings of the electronic monitor.

Referring now to FIG. 16 with reference to FIGS. 1-10, the internal workings of the electronic monitor 8 are provided. Monitor 8 is plugged into commercial power and/or batteries are installed. After module 6 is charged, module 6 is removed from charging circuit 34 and snapped into connector 4. Alarm values are set via adjustment buttons on the outside of monitor 8. Monitor 8 establishes connection with module 6. The firmware causes the 802.15.4 radio to accept communication that conforms to the correct protocol. The monitor 8 receives data from module 6. The firmware causes the display to show the corresponding value. Monitor 8 displays the temperature value. An alarm is sounded if the display values are equal to or greater than the alarm values. The display values are recorded in a memory buffer for later retrieval. An outside storage device can be attached to the port on monitor 8 to extract the stored data.

Although the foregoing detailed description has been set forth in some detail by way of illustration and example for purposes of clarity of understanding, it will be obvious that certain changes and modifications can be made within the full scope of the invention.

I claim:

1. An apparatus comprising:

a garment;

at least one sensor positioned in said garment to obtain a temperature reading of a wearer of said garment;

means to electronically connect said at least one sensor to an at least one connector;
least one connector comprising:
an insertion portion with connection pads configured to connect to a receiver;
a noninsertion portion with solder points for connecting to said at least one sensor;
a water proof housing covering said solder points; and
means to permanently attach said connector to said garment;
an electronic transmission module comprising a receiver configured to connect with said plurality of connective pads.

2. The apparatus of claim 1 further comprising an electronic monitor to remotely receive and control electronic transmission from said electronic transmission module.

3. The apparatus of claim 2 wherein said electronic monitor comprises a device wherein said device conforms to the IEEE 802.15.4 Low-Rate Wireless Personal Area Standard.

4. The apparatus of claim 1 wherein said electronic transmission module comprises a device wherein said device conforms to the IEEE 802.15.4 Low-Rate Wireless Personal Area Standard.

5. The apparatus of claim 1 further comprising a means to extend electronic transmission range of said electronic transmission module.

6. The apparatus of claim 5 wherein said means to extend electronic transmission range of said electronic transmission module is a range extender.

7. The apparatus of claim 6 wherein said range extender comprises a device, wherein said device conforms to the IEEE 802.15.4-2003 Low-Rate Wireless Personal Area Standard.

8. A method for monitoring the body temperature of an individual, the method comprising the steps of:
placing the garment of claim 1 on an individual;
determining a body temperature from said sensor;
communicating the body temperature from the individual to an electronic monitor over a local wireless connection, wherein said electronic monitor is configured to remotely receive and control electronic transmission from said electronic transmission module; and
displaying the body temperature on said electronic monitor.

9. The method of claim 8 further comprising the step of extending electronic transmission range between the electronic transmission module and the electronic monitor with a range extender.

10. The method of claim 8 further comprising the step of announcing the body temperature of said electronic monitor.

* * * * *